US005985320A

United States Patent [19]
Edwards et al.

[11] Patent Number: 5,985,320
[45] Date of Patent: *Nov. 16, 1999

[54] MATERIALS AND METHODS FOR ENHANCING CELLULAR INTERNALIZATION

[75] Inventors: David A. Edwards, State College; Daniel R. Deaver, Port Matilda, both of Pa.; Robert S. Langer, Newton, Mass.

[73] Assignee: The Penn State Research Foundation, University Park, Pa.

[ * ] Notice: This patent issued on a continued prosecution application filed under 37 CFR 1.53(d), and is subject to the twenty year patent term provisions of 35 U.S.C. 154(a)(2).

[21] Appl. No.: 08/810,275

[22] Filed: Mar. 3, 1997

Related U.S. Application Data

[60] Provisional application No. 60/012,721, Mar. 4, 1996.
[51] Int. Cl.⁶ .................................................. A61K 9/127
[52] U.S. Cl. ......................... 424/450; 424/427; 424/430; 424/434; 424/435; 424/436; 424/489; 436/829; 935/54
[58] Field of Search ..................................... 424/400, 450, 424/427–436, 489–502; 436/829; 935/54

[56] References Cited

U.S. PATENT DOCUMENTS

| 5,258,499 | 11/1993 | Konigsberg et al. |
|---|---|---|
| 5,344,644 | 9/1994 | Igai ........................................ 424/85.1 |
| 5,399,351 | 3/1995 | Leshchine .............................. 424/422 |

OTHER PUBLICATIONS

*Concise Encyclopedia of Polymer Science and Polymeric Amines and Ammonium Salts*, E. Goethals, editor (Pergamen Press, Elmsford, NY 1980).
Edwards et al., "Spontaneous Vesicle Formation at Lipid Bilayer Membranes," *Biophys. J.* 71:1208–1214 (1996).
Evans and Young, "Apparent Viscosity and Cortical Tension of Blood Granulocytes Determined by Micropipet Aspiration," *Biophys. J.*, 56:151–160 (1989).
Goldstein, J.L., et al., "Receptor–Mediated Endocytosis: Concepts Emerging from t he LDL Receptor System," *Ann. Rev. Cell Biol.* 1:1–39 (1985).
McGraw, T.E., et al., "Functional Expression of the Human Transferrin Receptor cDNA in Chinese Hamster Ovary Cells Deficient in Endogenous Transferrin Receptor," *J. Cell Biol.* 105:207–214 (1987).
Pagano, R.E., "Lipid Traffic in Eukaryotic Cells: Mechanisms for Intracellular Transport and Organelle–Specific Enrichment of Lipids," *Curr. Op. Cell Biol.* 2:652–663 (1990).

(List continued on next page.)

*Primary Examiner*—Gollamudi S. Kishore
*Attorney, Agent, or Firm*—Thomas J. Monahan

[57] ABSTRACT

Compositions and methods for delivering agents across cell membranes are disclosed. The compositions include an agent to be delivered, a viscous material, such as a hydrogel, lipogel or viscous sol, and, optionally, a carrier that includes a ligand that binds to or interacts with cell surface receptors. The agent to be delivered binds to or otherwise interacts with cell surface receptors, is attached, either covalently or ionically to a molecule that binds to or interacts with a cell surface receptor, or is associated with the carrier. Agents to be delivered include bioactive compounds and diagnostic agents. The compositions have an apparent viscosity roughly equal to the viscosity of the cytosol in the cell to which the agent is to be delivered. The rate of cellular internalization is higher when the viscosity of the viscous material and that of the cytosol in the cell are approximately the same, relative to when they are not the same. The compositions enhance cellular entry of bioactive agents and diagnostic materials when administered vaginally, nasally, rectally ocularly, orally, or to the respiratory or pulmonary system.

33 Claims, 7 Drawing Sheets

OTHER PUBLICATIONS

Rodman, T.S., et al., "Endocytosis and Transcytosis," *Curr. Op. Cell Biol.* 2:664–672 (1990).

Scartazzini et al., "Organogels from Lecithins," *Phys. Chem.,* 92:829–833 (1988).

Schmid, S.L., "Biochemical Requirements for the Formation of Clathrin–and COP–coated Transport Vesicles," *Curr. Op. Cell Biol.* 5:621–627 (1993).

Schonhorn and Wessling–Resnick, "Brefeldin A Down–Regulates the Transferrin Receptor in K562 Cells," *Molecular and Cellular Biochem.* 135:159–169 (1994).

Sheetz, M.P. and Dai, J., "Modulation of Membrane Dynamics and Cell Motility by Membrane Tension," presented at the 60th Annual Cold Spring Harbor Symposium on Protein Kinases, Cold Spring Harbor, N.Y. (1995).

Smythe, E., et al., "Formation of Coated Vesicles from Coated Pits in Broken A431 Cells," *J. Cell Biol.* 108:843–853 (1989).

Smythe, E. et al., "Cytosol–and Clathrin–dependent Stimulation of Endocytos in vitro by Purified Adaptors," *J. Cell Biol.* 119:1163–1171 (1992).

Trowbridge, I.S., "Endocytosis and Signals for Internalization," *Curr. Op. Cell Biol.* 3:634–641 (1991).

Wang et al., "Mechanotransduction Across the Cell Surface and Through the Cytoskeleton," *Science,* 260:1124–1126 (1993).

Wang, N. and Ingber, D.E., "Control of Cytoskeletal Mechanics by Extracellular Matrix," *Biophys. J.* 66:2181–2189 (1994).

MATERIALS AND METHODS FOR ENHANCING CELLULAR INTERNALIZATION

CROSS-REFERENCE TO RELATED APPLICATIONS

This application claims priority to provisional U.S. application Ser. No. 60/012,721, filed Mar. 4, 1996.

The United States government has certain rights in this invention by virtue of government support under Grant Number NIH-5R01-GM26698 awarded by the National Institutes of Health.

FIELD OF THE INVENTION

The compositions and methods of use described herein are in the area of materials and methods for enhancing cellular internalization.

BACKGROUND OF THE INVENTION

It is often difficult to deliver compounds, such as proteins, peptides, genetic material, and other drugs and diagnostic compounds intracellularly because cell membranes often resist the passage of these compounds. Various methods have been developed to administer agents intracellularly. For example, genetic material has been administered into cells in vivo, in vitro and ex vivo using viral vectors, DNA/lipid complexes and liposomes. While viral vectors are efficient, questions remain regarding the safety of a live vector and the development of an immune response following repeated administration. Lipid complexes and liposomes appear less effective at transfecting DNA into the nucleus of the cell and may potentially be destroyed by macrophages in vivo.

Proteins and peptides are typically administered by parenteral administration, or, in some cases, across the nasal mucous membrane. Uptake of drugs administered topically is frequently poor, and degradation frequently occurs when drugs are administered orally. For example, hormones such as gonadotropin releasing hormone ("GnRH") and its analogs have been administered to humans in an attempt to increase fertility by increasing systemic levels of luteinizing hormone ("LH"). When given often, low doses of native GnRH have been shown to induce follicular development and ovulation. These drugs are typically administered via an indwelling catheter into the abdominal cavity. An external pump is attached to the catheter which injects the peptide at frequent intervals. This method of administration is extremely invasive and undesirable. Also, the method is prohibitively expensive for use in animals.

The binding of ligands or assembly proteins to surface receptors of eucaryotic cell membranes has been extensively studied in an effort to develop better ways to promote or enhance cellular uptake. For example, binding of ligands or proteins has been reported to initiate or accompany a cascade of nonequilibrium phenomena culminating in the cellular invagination of membrane complexes within clathrin-coated vesicles [Goldstein, J. L., et al. (1985) *Ann. Rev. Cell Biol.* 1, 1–39; Rodman, T. S., et al. (1990) *Curr. Op. Cell Biol.* 2, 664–672; Trowbridge, I. S. (1991) *Curr. Op. Cell Biol.* 3, 634–641; Smythe, E., et al. (1989) *J. Cell Biol.* 108, 843–853; Smythe, E., et al. (1992) *J. Cell Biol.* 119, 1163–1171; and Schmid, S. L. (1993) *Curr. Op. Cell Biol.* 5, 621–627]. This process has been referred to as receptor-mediatedendocytosis (RME). Beyond playing a central role in cellular lipid trafficking [Pagano, R. E. (1990) *Curr. Op. Cell Biol.* 2, 652–663], RME is the primary means by which macromolecules enter eucaryotic cells. Having a better understanding of the role of RME in uptake of drugs would be advantageous in developing improved methods of drug delivery.

It would be advantageous to have new methods for delivering agents intracellularly. It is therefore an object of the present invention to provide compositions and methods for enhancing intracellular delivery of bioactive and/or diagnostic agents. It is a further object of the present invention to provide less invasive methods for delivering high molecular weight and labile drugs, such as proteins and nucleic acid molecules, and diagnostic agents.

SUMMARY OF THE INVENTION

Compositions and methods for improving cellular internalization of one or more compounds are disclosed. The compositions include a compound to be delivered and a biocompatible viscous material, such as a hydrogel, lipogel or highly viscous sol. By controlling the apparent viscosity of the viscous materials, the rates of endocytosis, including nonspecific "pinocytosis" and specific receptor mediated endocytosis ("RME"), are increased. The rate of endocytic internalization is increased when the ratio of the apparent viscosities of cytosolic and extracellular media approaches unity. This leads to high transport rates of compounds to be delivered across cell membranes, facilitating more efficient delivery of drugs and diagnostic agents.

Preferred viscous materials are hydrogels, lipogels (gels with nonaqueous fluid interstices) and highly viscous sols. The apparent viscosity of the composition is controlled such that it lies in the range of between 0.1 and 2000 Poise, preferably between 7 and 1000 Poise, and most preferably between 2 and 200 Poise.

Compounds to be delivered include those that can be attached, covalently or noncovalently, to a molecule that either stimulates RME or pinocytosis by binding to receptors on the plasma membrane, binds specifically to receptors that undergo RME or pinocytosis independently of this binding, or at least can be associated chemically or physically with other molecules or "carriers" that themselves undergo RME or pinocytosis. Exemplary compounds to be delivered include proteins and peptides, nucleotide molecules, saccharides and polysaccharides, synthetic chemotherapeutic agents and diagnostic compounds.

The compositions are applied to cell membranes to achieve high rates of drug transport across those membranes, relative to when non-viscous fluids are used. Methods for administering the compositions include application topically or by injection. Compositions can be applied topically orally, nasally, vaginally, rectally and ocularly. Compositions can be applied by injection via catheter, intramuscularly, subcutaneously, or intraperitoneally. Compositions can also be administered to the pulmonary or respiratory system, most preferably in an aerosol.

The examples demonstrate the administration of transferrin to single cells to enhance the rate of transferrin uptake and the intravaginal administration of leuprolide to increase LH levels in sheep.

DETAILED DESCRIPTION OF THE INVENTION

Figure 1:
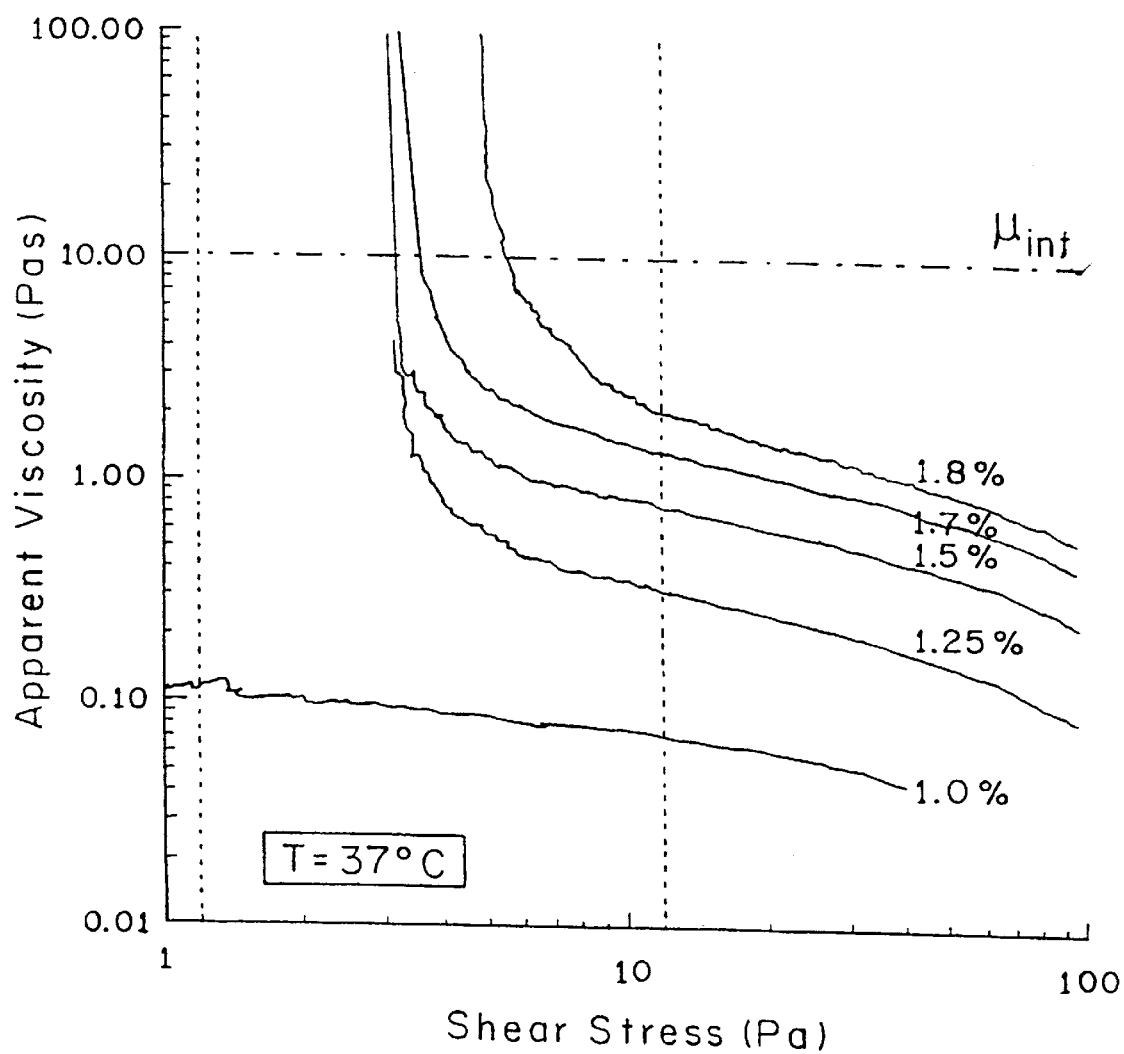
FIG. 1 shows apparent viscosity versus applied shear stress for various methocel solutions (0, 1, 1.25, 1.5, 1.7, and 1.8%). A characteristic value of the cell viscosity is shown. The vertical dashed lines represent estimates of the maximum and minimum force values delivered by a cell on the extracellular fluid by invaginating pits.

Compositions and methods for intracellular delivery of compounds in a viscous solution enhancing uptake are described. Cellular internalization is enhanced by increasing the rate of endocytosis, particularly receptor-mediated endocytosis, by controlling the viscosity of the solution. The compositions include one or more bioactive or diagnostic compounds and a fluid with an apparent viscosity approximately equal to the apparent viscosity of the cytosolic fluid in the cell to which the composition is administered.

Preferably, the compound binds to or otherwise interacts with receptors on the surface of the cell to which it is to be delivered. If the compound does not itself bind to or interact with receptors on the cell surface, it can be administered in a viscous fluid that also includes a carrier for the compound. The carrier contains ligands that bind to or otherwise interact with cell surface receptors, which allows compounds that do not bind to or otherwise interact with cell surface receptors to participate in RME.

Compositions

The binding of ligands or assembly proteins to surface receptors of eucaryotic cell membranes initiates or accompanies a cascade of nonequilibrium phenomena culminating in the cellular invagination of membrane complexes within clathrin-coated vesicles. This process is known as receptor-mediated endocytosis (RME). RME is the primary means by which several types of bioactive molecules, particularly macromolecules, enter eukaryotic cells.

Research by others has primarily focused on the identification and biochemical characterization of the early and later stages of RME, ranging from formation of a clathrin coated pit to snap-off of a coated vesicle. Determination of the compositions and methods for intracellularly administering compounds described herein involved focusing on a different aspect of RME, the process in which a membrane depression is initially formed at the outset of RME (i.e. the mechanism by which a spontaneous thrust of the cell membrane toward the cytosol occurs). This process is referred to herein as the 'nucleation stage' of RME. This terminology is intended to emphasize that the driving force for the spontaneous thrust of the membrane toward the cytosol is related to energy liberated by one or more of many possible exothermic membrane-binding reactions, i.e., receptor-ligand binding, that precede or accompany formation of a membrane depression.

Cell membranes are bound from without by extracellular fluid and from within by cytosolic fluid. The inter- and extracellular fluids possess different physical properties, such as density and fluid viscosity, whose values extend up to the membrane surface where they undergo discontinuities. The membrane itself possesses unique equilibrium and nonequilibrium properties. An important property when considering intracellular delivery is the membrane tension (the free energy of the membrane per unit surface area). Membrane tension is generally uniform and positive at an equilibrium membrane and can be measured by routine micropipet experiments. Most reported membrane tension values have been gathered for red blood cells, and range from 4 dyne/cm to 0.01 dyne/cm. By contrast, the interfacial tension of an air/water interface is 73 dyne/cm. Membrane tension can vary from point to point on the membrane surface as a consequence of various stimuli, such as non-uniform heating of the membrane, membrane chemical reactions and membrane compositional changes. These variations can give rise to membrane and bulk-fluid motion, termed Marangoni convection. This motion is characterized for the most part by cytosolic and extracellular (apparent) viscosities.

Exothermic reactions can occur on the cell membrane, due to ligand-receptor binding, adaptor-membrane binding, clathrin-membrane binding, a combination of these binding reactions, and other membrane reactions. The exothermic reactions cause the membrane tension (energy per membrane area), at least momentarily, to be diminished at the point where the reaction occurred. As the membrane tension is lowered, the configurational and intermolecular potential energies of membrane-bound molecular complexes are also lowered.

The cell membrane tension is spatially nonuniform as a consequence of the exothermic reactions (i.e., membrane complex formation), resulting in membrane motion. This motion will possess a substantial component toward the cell cytosol so long as the cytosolic viscosity exceeds that of the extracellular fluid.

This membrane motion causes membrane deformation, an event resisted by the membrane tension. When the differences between the apparent viscosities of the cytosolic fluid and the extracellular fluid are extremely large, membrane deformation is strongly resisted and the initial thrust of the membrane is damped. However, as the differences between the apparent viscosities of the cytosolic fluid and the extracellular fluid become extremely small, membrane deformation becomes progressively rapid.

Figure 3:
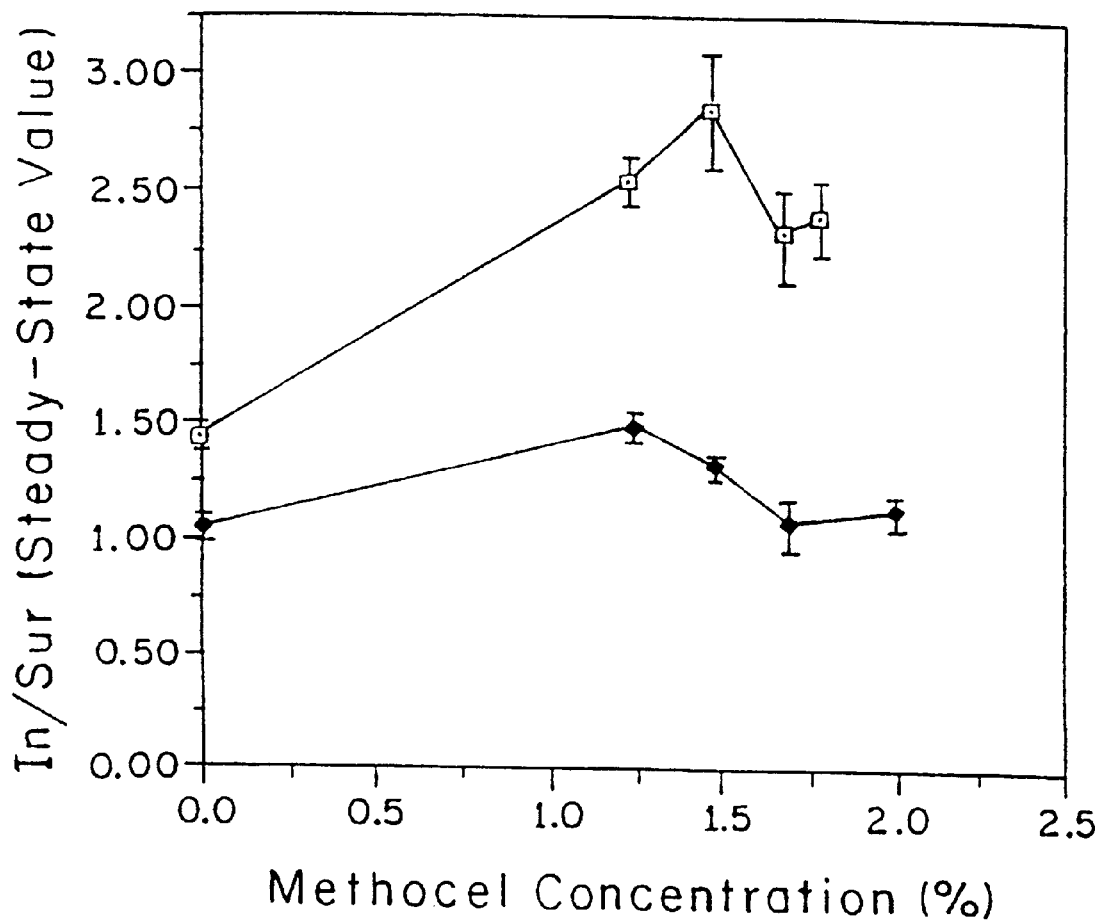
FIG. 3 shows steady-state values of total internalized $^{125}$I-Tf over total surface-associated $^{125}$I-Tf (In/Sur) for CHO cells suspended (top line with open blocks) and adhered (bottom line with closed blocks) in methocel solutions of varying methocel concentration. Error bars represent mean standard error, with n=4.
Figure 4:
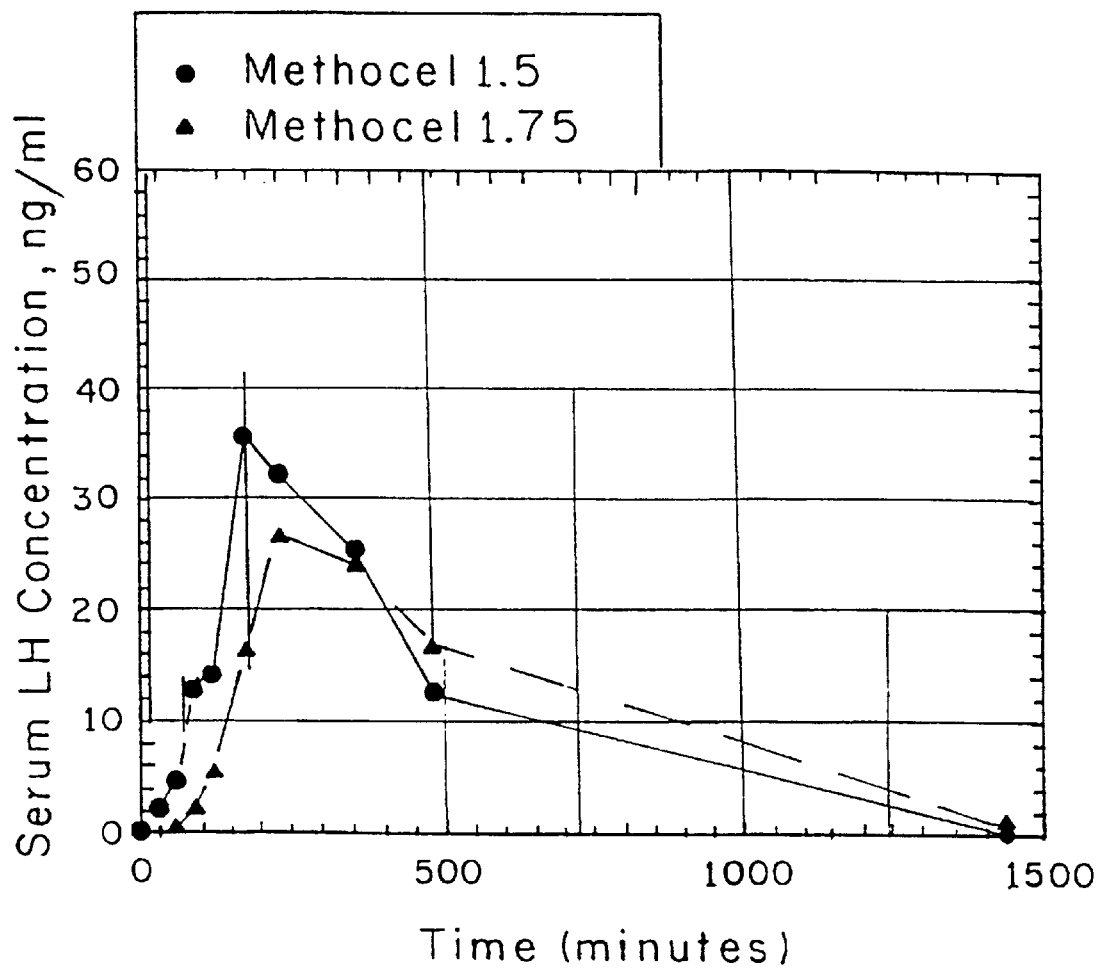
FIG. 4 shows the systemic concentration of LH following intravaginal administration to sheep of leuprolide in 1.5% and 1.75% methocel solutions.
Figure 5:
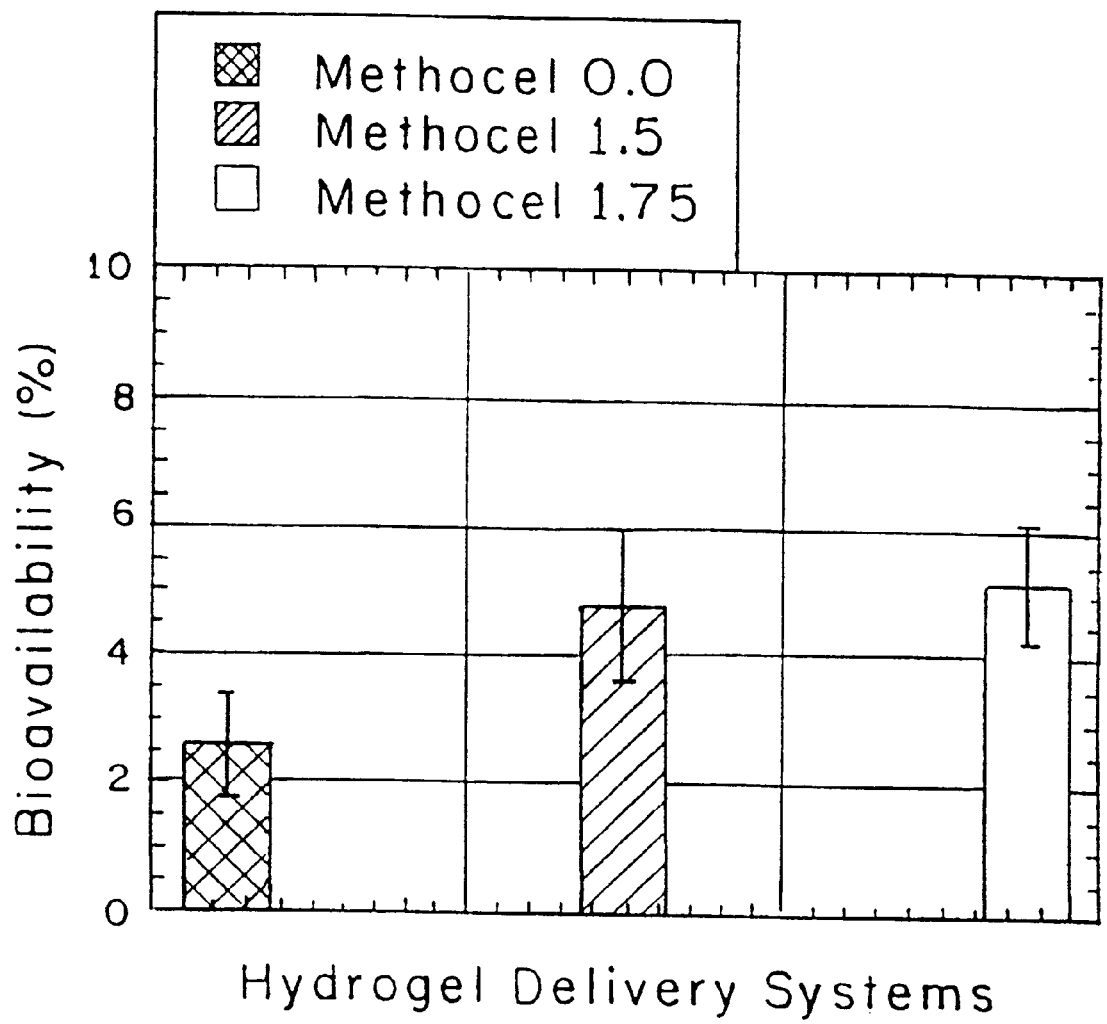
FIG. 5 shows absolute leuprolide bioavailability (percent bioavailability) of rheologically-optimized hydrogel delivery systems (1.5 and 1.75% methocel) compared to a control hydrogel delivery system.
Figure 6:
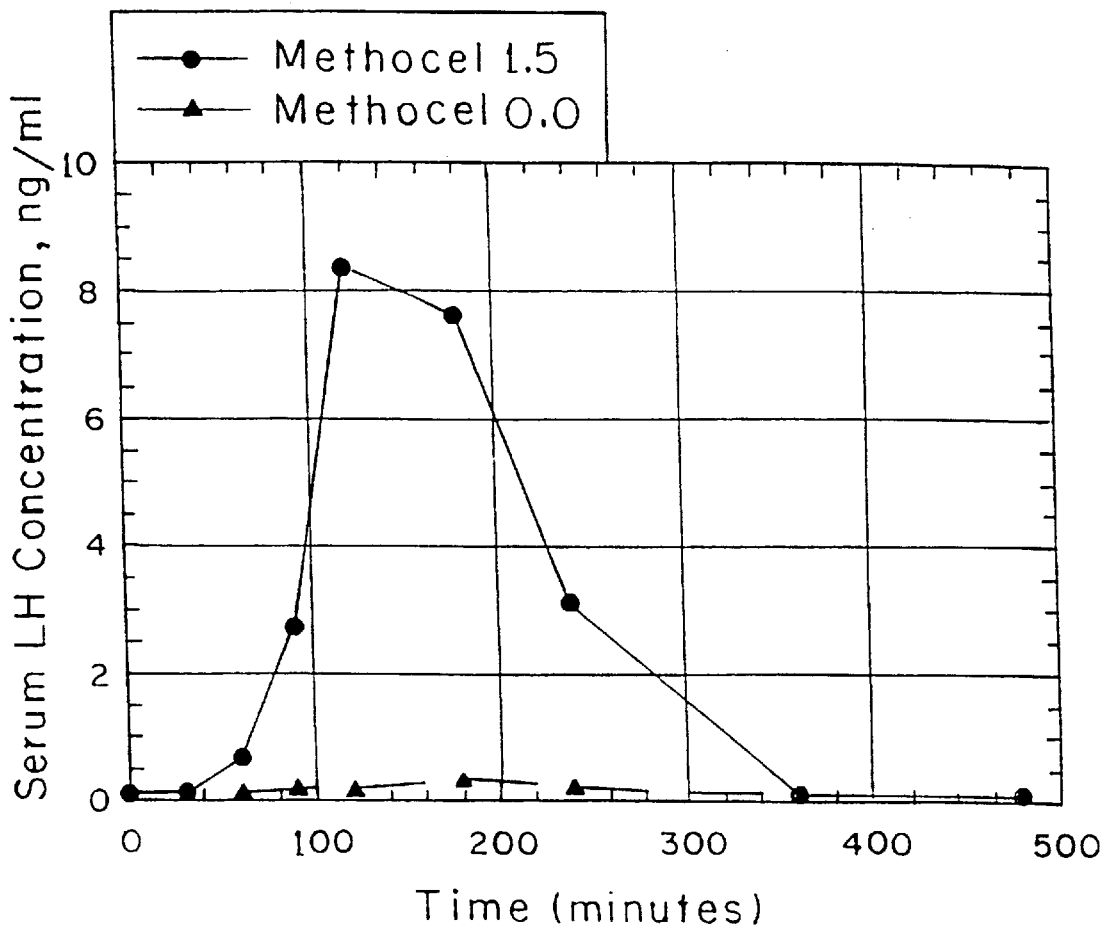
FIG. 6 shows the systemic concentration of LH following intranasal administration of 100 μg of leuprolide acetate in 1.5% methocel and 0.0% methocel (saline control) to sheep.
Figure 7:
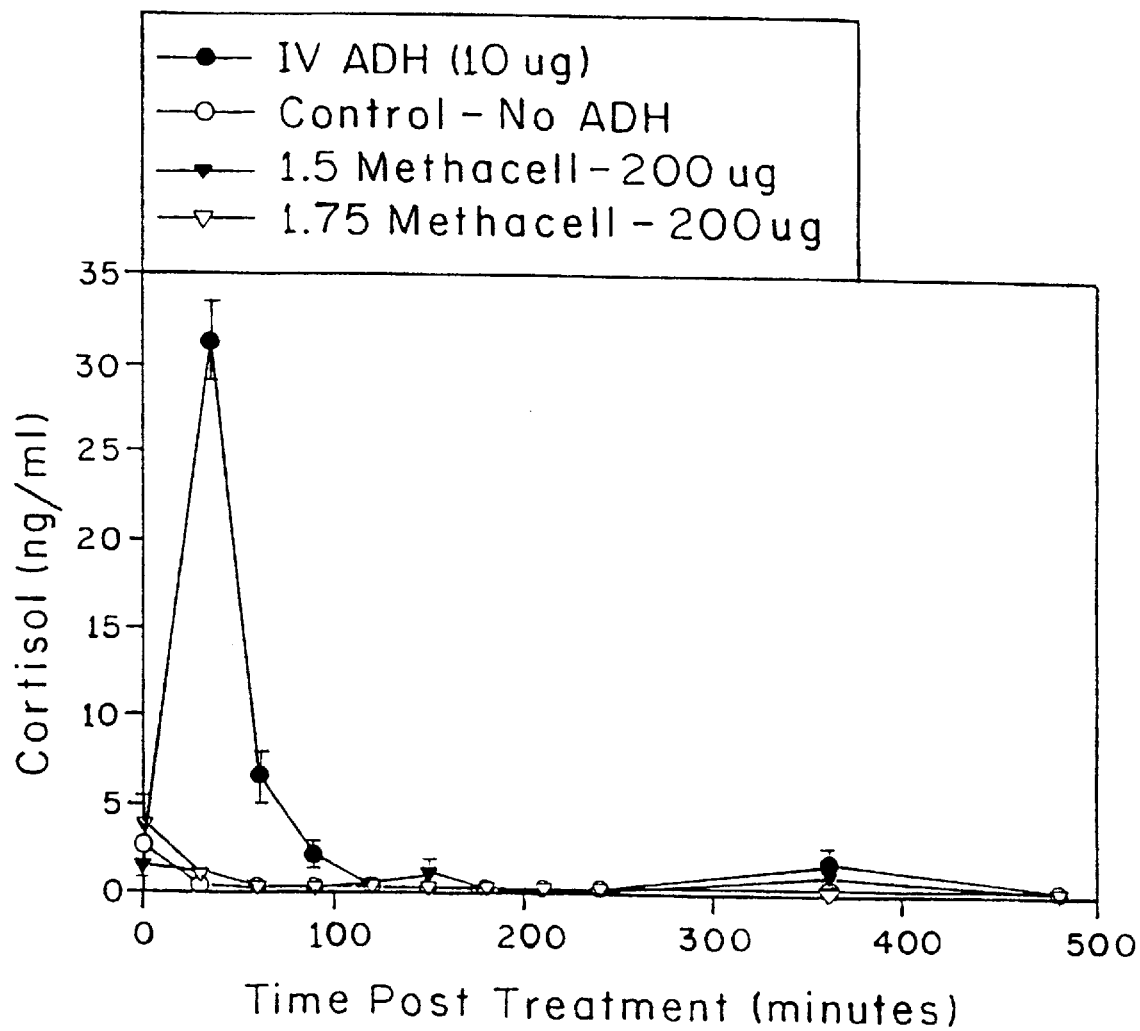
FIG. 7 shows the systemic concentration of cortisol (ng/mL) following intravenous and intravaginal administration of vasopressin to sheep. The darkened circles represent IV administration (10 micrograms vasopressin) without a viscous carrier. The empty circles represent the control, with no viscous gel or vasopressin. The darkened triangles represent intravaginal administration of 200 μg vasopressin in 1.5% methocel. The empty triangles represent intravaginal administration of 200 μg vasopressin in 1.75% methocel.

Accordingly, the rate of endocytosis can be increased by adjusting the viscosity of the extracellular fluid so that it is approximately the same as that of the cytosolic fluid. If the viscosity of the extracellular fluid is appreciably higher or lower than that of the cytosolic fluid, the rate of endocytosis decreases. This was shown experimentally in Example 1 and FIG. 3, in which the ratio of compounds that were internalized to those remaining on the surface (In/Sur) increased as the viscosity of the extracellular fluid increased, to a point at which the viscosity approached that of the cytosolic fluid. Above that value, the ratio decreased.

Clustering of membrane complexes is favorable for rapid internalization. The rate of internalization can be increased in proportion to the magnitude of binding energy. This is due, in part, to the specificity of receptors to particular ligands and/or adaptor proteins.

Clustering of complexes occurs in the vicinity of pits to which clathrin triskelions absorb from the cytosolic side of the cell membrane and subsequently polymerize to form a clathrin coat. Some clustering has also been observed in the vicinity of caveolae, or non-clathrin-coated pits. The membrane-tension depression occurring within the vicinity of an evolving pit, originating in the process of membrane complexation, is directly proportional to the number of membrane complexes formed within that pit. In general, clustered complexes have been found to internalize substances more rapidly than nonclustered complexes.

The magnitudes of apparent viscosity difference and receptor clustering have each been found to alter the rate of RME. Membrane tension can also be manipulated to influence the rate of RME. Increasing the membrane tension 'hardens' the cell membrane, making cell membrane depression increasingly prohibitive. This phenomenon has been commented upon by Sheetz, M. P. and Dai, J. (1995), presented at the 60th *Annual Cold Spring Harbor Symposium on Protein Kinases*, Cold Spring Harbor, N.Y., on the basis of studies that show an increased rate of endocytosis for neuronal growth cones coinciding with membrane tension lowering.

Accordingly, the rate of internalization can be increased by a) adjusting the viscosity of the extracellular fluid to approximate that of the cytosolic fluid; b) forming complexes of the material to be internalized; and c) reducing membrane tension. Compositions and methods for increasing the rate of endocytosis are described in detail below.

A. Viscous Hydrogels

Suitable viscous fluids for use in intracellularly administering compounds include biocompatible hydrogels, lipogels, and highly viscous sols.

A hydrogel is defined as a substance formed when an organic polymer (natural or synthetic) is cross-linked via covalent, ionic, or hydrogen bonds to create a three-dimensional open-lattice structure which entraps water molecules to form a gel. Examples of materials which can be used to form a hydrogel include polysaccharides, proteins and synthetic polymers. Examples of polysaccharides include celluloses such as methyl cellulose, dextrans, and alginate. Examples of proteins include gelatin and hyaluronic acid. Examples of synthetic polymers include both biodegradeable and non-degradeable polymers (although biodegradeable polymers are preferred), such as polyvinyl alcohol, polyacrylamide, polyphosphazines, polyacrylates, polyethylene oxide, and polyalkylene oxide block copolymers ("poloxamers™") such as Pluronics™ or Tetronics™ (polyethylene oxide-polypropylene glycol block copolymers).

In general, these polymers are at least partially soluble in aqueous solutions, such as water, buffered salt solutions, or aqueous alcohol solutions. Several of these have charged side groups, or a monovalent ionic salt thereof. Examples of polymers with acidic side groups that can be reacted with cations are polyphosphazenes, polyacrylic acids, poly(meth)acrylic acids, polyvinyl acetate, and sulfonated polymers, such as sulfonated polystyrene. Copolymers having acidic side groups formed by reaction of acrylic or methacrylic acid and vinyl ether monomers or polymers can also be used. Examples of acidic groups are carboxylic acid groups, sulfonic acid groups, halogenated (preferably fluorinated) alcohol groups, phenolic OH groups, and acidic OH groups.

Examples of polymers with basic side groups that can be reacted with anions are polyvinyl amines, polyvinyl pyridine, polyvinyl imidazole, polyvinylpyrrolidone and some imino substituted polyphosphazenes. The ammonium or quaternary salt of the polymers can also be formed from the backbone nitrogens or pendant imino groups. Examples of basic side groups are amino and imino groups.

Alginate can be ionically cross-linked with divalent cations, in water, at room temperature, to form a hydrogel matrix. An aqueous solution containing the agent to be delivered can be suspended in a solution of a water soluble polymer, and the suspension can be formed into droplets which are configured into discrete microcapsules by contact with multivalent cations. Optionally, the surface of the microcapsules can be crosslinked with polyamino acids to form a semipermeable membrane around the encapsulated materials.

The polyphosphazenes suitable for cross-linking have a majority of side chain groups which are acidic and capable of forming salt bridges with di- or trivalent cations. Examples of preferred acidic side groups are carboxylic acid groups and sulfonic acid groups. Hydrolytically stable polyphosphazenes are formed of monomers having carboxylic acid side groups that are crosslinked by divalent or trivalent cations such as $Ca^{2+}$ or $Al^{3+}$. Polymers can be synthesized that degrade by hydrolysis by incorporating monomers having imidazole, amino acid ester, or glycerol side groups. For example, a polyanionic poly[bis(carboxylatophenoxy)] phosphazene (PCPP) can be synthesized, which is cross-linked with dissolved multivalent cations in aqueous media at room temperature or below to form hydrogel matrices.

Methods for the synthesis of the polymers described above are known to those skilled in the art. See, for example *Concise Encyclopedia of Polymer Science* and *Polymeric Amines and Ammonium Salts*, E. Goethals, editor (Pergamen Press, Elmsford, N.Y. 1980). Many of these polymers are commercially available.

Preferred hydrogels include aqueous-filled polymer networks composed of celluloses such as methyl cellulose, dextrans, agarose, polyvinyl alcohol, hyaluronic acid, polyacrylamide, polyethylene oxide and polyoxyalkylene polymers ("poloxamers"), especially polyethylene oxide-polypropylene glycol block copolymers, as described in U.S. Pat. No. 4,810,503. Several poloxamers are commercially available from BASF and from Wyandotte Chemical Corporation as "Pluronics". They are available in average molecular weights of from about 1100 to about 15,500.

As used herein, lipogels are gels with nonaqueous fluid interstices. Examples of lipogels include natural and synthetic lecithins in organic solvents to which a small amount of water is added. The organic solvents include linear and cyclic hydrocarbons, esters of fatty acids and certain amines (Scartazzini et al. (1988) *Phys. Chem.*, 92, 829–833).

As defined herein, a sol is a colloidal solution consisting of a liquid dispersion medium and a colloidal substance which is distributed throughout the dispersion medium. A highly viscous sol is a sol with a viscosity between approximately 0.1 and 2000 Poise.

Other useful viscous fluids include gelatin and concentrated sugar (such as sorbitol) solutions with a viscosity between approximately 0.1 and 2000 Poise.

The apparent viscosity of the extracellular fluid (the composition) must be approximately equal to the viscosity of the cytosolic fluid in the cell to which the compounds are to be administered. One of skill in the art can readily determine or arrive at a reasonable estimate of the viscosity of the cytosolic fluid using a viscometer and measuring the applied stress divided by measured strain rate at the applied stress that corresponds to the stress the cell membrane imparts upon the cytosolic and extracellular fluids during endocytosis. Methods for measuring the cytosolic viscosity include micropipette methods (Evans and Young, *Biophys. J.*, 56:151–160 (1989)) and methods involving the motion of membrane-linked colloids (Wang et al., *Science*, 260:1124–1126 (1993). Typical cytosol viscosities, measured by these techniques, range from approximately 50–200 Poise. Once this value is measured, the viscosity of the composition can be adjusted to be roughly equal to that viscosity, particularly when measured via routine methods at the applied stress that corresponds to the stress the cell membrane imparts upon the cytosolic and extracellular fluids during endocytosis.

The viscosity can be controlled via any suitable method known to those of skill in the art. The method for obtaining a viscous composition with the desired apparent viscosity is not particularly limited since it is the value of the apparent viscosity relative to the target cells which is critical. The apparent viscosity can be controlled by adjusting the solvent (i.e., water) content, types of materials, ionic strength, pH, temperature, polymer or polysaccharide chemistry performed on the materials, and/or external electric, ultrasound, or magnetic fields, among other parameters.

The apparent viscosity of the compositions is controlled such that it lies in the range of between 0.1 and 2000 Poise, preferably between 7 and 1000 Poise, and most preferably between 2 and 200 Poise. The apparent viscosity can be measured by a standard rheometer using an applied stress range of between 1 and 1000 Pascals, preferably between 1 and 500 Pascals, and most preferably between 1 and 100 Pascals. Further, the viscosity of the compositions is controlled so that the quotient of (apparent viscosity of the cytosol of the target cells—apparent viscosity of the composition) and the apparent viscosity of the cytosol of the target cells is between approximately −0.1 and 0.3, preferably between approximately 0 and 0.3, more preferably between approximately 0 and 0.1, and most preferably between approximately 0 and 0.05.

The composition can be administered as an only slightly viscous formulation that becomes more viscous in response to a condition in the body, such as body temperature or a physiological stimulus, like calcium ions or pH, or in response to an externally applied condition, such as ultrasound or electric or magnetic fields. An example is a temperature sensitive poloxamer which increases in viscosity at body temperature.

The following are examples of suitable concentration ranges: Methylcellulose (methocel) solutions in the range of between 1.0 and 2.0% (w/w), polyvinyl alcohol solutions between 5 and 15%, pluronic acid solutions between 15 and 20% and trehalose solutions between 1 and 5%.

B. Compounds to be Delivered

Compounds that can be attached, covalently or noncovalently, to a molecule that either stimulates receptor-mediated endocytosis (RME) or pinocytosis by binding to receptors on the plasma membrane, binds specifically to receptors that undergo RME or pinocytosis independently of this binding, or at least can be associated chemically or physically with other molecules or "carriers" that themselves undergo RME or pinocytosis, can be intracellularly delivered using the compositions and methods described herein.

Suitable compounds include proteins and peptides, nucleic acid molecules including DNA, RNA, antisense oligonucleotides, triplex forming materials, ribozymes, and guide sequences for ribozymes, carbohydrates and polysaccharides, lipids, and other synthetic organic and inorganic molecules. Preferred bioactive compounds include growth factors, antigens, antibodies or antibody fragments, and genes such as genes useful for treatment of cystic fibrosis, A1A deficiency and other genetic deficiencies.

Preferred hormones includes peptide-releasing hormones such as insulin, luteinizing hormone releasing hormone ("LHRH"), gonadotropin releasing hormone ("GnRH"), deslorelin and leuprolide acetate, oxytocin, vasoactive intestinal peptide (VIP), glucagon, parathyroid hormone (PTH), thyroid stimulating hormone, follicle stimulating hormone, growth factors such as nerve growth factor (NGF), epidermal growth factor (EGF), vascular endothelial growth factor (VEGF), insulin-like growth factors (IGF-I and IGF-II), fibroblast growth factors (FGFs), platelet-derived endothelial cell growth factor (PD-ECGF), transforming growth factor beta (TGF-β), and keratinocyte growth factor (KGF). Other materials which can be delivered include cytokines such as tumor necrosis factors (TFN-α and TNF-β), colony stimulating factors (CSFs), interleukin-2, gamma interferon, consensus interferon, alpha interferons, beta interferon; attachment peptides such as RGD; bioactive peptides such as renin inhibitory peptides, vasopressin, detirelix, somatostatin, and vasoactive intestinal peptide; coagulation inhibitors such as aprotinin, heparin, and hirudin; enzymes such as superoxide dismutase, neutral endopeptidase, catalase albumin, calcitonin, alpha-1-antitrypsin (A1A), deoxyribonuclease (DNAase) lectins such as concanavalin A, and analogues thereof.

Diagnostic agents can also be delivered. The se can be administe red alone or coupled to one or more bioactive compounds as described above. The agents can be radiolabelled, fluorescently labelled, enzymatically labelled and/or include magnetic compounds and other materials that can be detected using x-rays, ultrasound, magnetic resonance imaging ("MRI"), computed tomagraph ("CT"), or fluoroscopy.

C. Carriers for Compounds to be Delivered

The compounds to be delivered can optionally be incorporated into carriers, which are then dispersed in a viscous fluid with an apparent viscosity approximately equal to the cytosolic fluid of the cell to which the compounds are to be delivered. Exemplary carriers include viruses, liposomes, lipid/DNA complexes, micelles, protein/lipid complexes, and polymeric nano- or microparticies.

The carrier must be small enough to be effectively endocytosed. Suitable carriers possess a characteristic dimension of less than about 200 nm, preferably less than about 100 nm, and more preferably, are less than about 60 nm.

The carrier must be able to bind to a cell surface receptor. If the carrier does not naturally bind, it is well known in the art how to modify carriers such that they are bound, ionically or covalently, to a ligand (i.e., LHRH) that binds to a cell surface receptor. For example, th U.S. Pat. No. 5,258,499 to Konigsberg et al. describes the incorporation of receptor specific ligands into liposomes, which are then used to target receptors on the cell surface.

The use of carriers can be important when the compound to be delivered does not bind to or otherwise interact with cell surface receptors. The compound can be incorporated into a carrier which contains a ligand or other moiety which binds to or interacts with cell surface receptors. Then, due to the binding of or interaction with the receptor to the cell surface and the apparent viscosity of the composition, the carrier (and encapsulated compound) is intracellularly delivered by endocytosis.

The use of carriers can be particularly important for intracellularly delivering nucleic acid molecules. In one embodiment, nucleic acid molecules are encapsulated in a liposome, preferably a cationic liposome, that has a receptor-binding ligand, such as LHRH, on its surface. The liposome is then dispersed in a viscous fluid. When the composition is administered, the liposomes are endocytosed by the cell, and the nucleic acid molecules are released from the liposome inside the cell.

Methods of Administration

The compositions can be applied topically to the vagina, rectum, nose, eye, ear, mouth and the respiratory or pulmonary system, or systemically to other types of cells, i.e., by intramuscular, subcutaneous, and intraperitoneal delivery. Preferably, the compositions are applied directly to the epithelial cell to which the compound is to be delivered.

The compositions are particularly advantageous for gene delivery and hormone therapy. By delivering a composition containing peptides such as GnRH or its analogues across the vaginal or nasal membranes the compositions can be used to treat a variety of human hormone-based disorders. Examples 2 and 3 demonstrate the efficacy of the compositions to increase LH levels when a composition including leuprolide was applied to the vaginal or nasal membranes.

The dosage will be expected to vary depending on several factors, including the patient, the particular bioactive compound to be delivered, and the nature of the condition to be treated, among other factors. One of skill in the art can readily determine an effective amount of the bioactive compound or compounds to administer to a patient in need thereof.

The method involves administering the composition to cells to enhance the rate of drug transport across the cell membranes, relative to the rate of delivery when non-viscous fluids are used. Examples of methods of administration include oral administration, as in a liquid formulation or within solid foods, topical administration to the skin or the surface of the eye, intravaginal administration, rectal administration, intranasal administration, administration via inhalation, administration via a catheter, and administration via intraperitoneal, intramuscular, or subcutaneous injection.

When the composition is administered orally or by inhalation, it is preferred that it is administered as a dry powder that includes a swellable hydrogel that is designed to swell to an appropriate viscosity after delivery to the desired location. After inhalation, for example, the hydrogel absorbs water to obtain the desired viscosity and then delivers agents to the respiratory system. When administered orally, a hydrogel can be selected that does not absorb water under conditions present in the upper gastrointestinal tract, but which does absorb water under conditions present in the lower gastrointestinal tract (i.e., at a pH greater than about 6.5). Such hydrogels are well known to those of skill in the art. The use of such compositions can optimize the delivery of agents to the lower gastrointestinal tract.

Methods for Lowering or Raising Membrane Tension

The efficiency of the method can be increased by lowering the membrane tension. Suitable methods for lowering membrane tension include including a biocompatible surface active agent in the hydrogel, performing exothermic reactions on the cell surface (i.e., complex formation), and applying an external field to the cell surface. Suitable biocompatible surface active agents include surfactin, trehalose, fatty acids such as palmitin and oleic acid, polyethylene glycol, hexadecanol, and phospholipids such as phosphatidylcholines and phosphatidylglycerols. Suitable complex-forming chemical reactions include the reaction of receptor-binding ligands with cell surface receptors for these ligands, exothermic reactions such as occur between sodium salicylate and salicylic acid, and neutralization reactions as between hydrochloric acid and ammonia (Edwards et al. 1996 *Biophys. J.* 71, 1208–1214). External fields that can be applied to a cell surface to reduce membrane tension include ultrasound, electric fields, and focused light beams, such as laser beams.

Methods for Causing the Clustering of Receptors

The rate of cellular internalization can also be increased by causing the clustering of receptors on the cell membrane. This can be accomplished, for example, by creating zones on the membrane where the membrane tension is relatively high, causing the membrane fluid to flow toward the zone of high membrane tension. This flow can carry receptors localized in the membrane toward each other, causing them to cluster.

The criteria for assessing response to therapeutic modalities employing an identified compound is dictated by the specific condition and will generally follow standard medical practices. Such an assessment can be made by determining if there is a desired effect, such as expression of a nucleotide molecule, production of a protein, or a consequent physiological effect. Where the administered compound is known or suspected to involve the function or expression of another molecule involved in a disease condition, the effectiveness of administration of the compound can be assessed by measuring changes in characteristics of the disease condition.

The compositions and methods of use thereof described herein will be more clearly understood with reference to the following examples:

EXAMPLE 1

Viscous Hydrogels with Optimum Viscosity for Cellular Internalization

Materials and Methods

Reagents. $^{125}$I labeled human transferrin was purchased from Amersham (Arlington Heights Ill.). All other chemicals, including human apo-transferrin and methyl cellulose (MW=80 KDa), were obtained from Sigma (St. Louis, Mo.).

Cell Culture and Preparation.

Human erythroleukemia K562 cells were grown in RPMI-1640 medium supplemented with 50 units/mL penicillin, 0.05 mg/mL streptomycin, 2 mM L-glutamine, and 10% fetal bovine serum. Chinese hamster ovary (CHO) cells transfected with human transferrin receptor, a generous gift from Dr. Timothy McGraw (Columbia University, New York, N.Y.), were grown in McCoy's 5A medium supplemented with 50 units/mL penicillin, 0.05 mg/mL streptonigrin, 2 mM L-Glutamine, and 5% fetal bovine serum.

Immediately before each experiment, all cells were washed two times with 40 mL ice cold buffer (25 mM Hepes, 150 mM NaCl, 1 mg/mL dextrose, and 1 mg/mL bovine serum albumin, pH 7.4), and centrifuged at 600 g at 4° C. for 10 minutes.

Methyl Cellulose Preparation and Characterization.

Methyl cellulose solutions were made in buffer with the dispersion technique formulated by Dow Chemical Co. to achieve a final concentration of 0.0 to 1.8%. Briefly, after one third volume of the buffer was heated to 90° C., methyl cellulose powder was added to the liquid and agitated until the particles were thoroughly wetted and evenly dispersed. The remainder of the buffer was then added to the methyl cellulose at 4° C. Agitation was maintained at 4° C. for another 20 minutes. One day before the experiments, $^{125}$I labeled transferrin (0.03 $\mu$Ci/mL) and nonlabeled transferrin (50 nM) were added to each concentration of methyl cellulose solution and thoroughly mixed.

The apparent viscosity of the methocel solutions was measured in a controlled stress rheometer (TA Instruments CSL-500) using a cone-and-plate geometry. All data shown in FIG. 1 have been obtained by exponentially reducing the externally imposed stress at a constant rate from 100 Pa to 1 Pa.

Endocytosis.

Steady-state ratios of total internalized transferrin to surface-bound transferrin were determined as follows: At 4° C., 2×10$^6$ cells were resuspended in 1 mL methyl cellulose solution (concentration ranging from 0.0 to 1.8%) containing radiolabeled and nonlabeled transferrin. A pasteur pipette was used to gently mix the cells and the methyl cellulose solution. Immediately after warming in a 37° C. water bath for 5 minutes, the samples were transferred to a 37° C. thermal hood, where slow rotation of the samples was maintained. After 1 hr, endocytosis was terminated by rapid addition of 12 mL ice cold Hank's balanced salt solution (HBSS), followed by 3 more washings of 12 mL ice cold HBSS and subsequent centrifugation (1200 g at 4° C.). After washing, cells were divided into two equal volumes. The cells from both sets of aliquots were pelleted. The samples from the first set were counted with a gamma counter (model 1274 Ria Gamma, LKB Wallac, Finland) to obtain the total radioactivity. The internal (In) and surface (Sur) radioactivity levels were determined from the second set of samples using the method of Schonhorn et al. [Schonhorn, J. E. and Wessling-Resnick, M. (1994) *Molecular and Cellular Biochem*. 135, 159–169]. Briefly, the pellets were incubated with 0.5 mL of trypsin solution (25 mM Hepes, 150 mM NaCl with 1mg/mL bovine trypsin, pH 7.4) at 4° C. The supernatants and the pellets were separated by centrifuging at 3000 g at 4° C. for 15 minutes. 2 mL of HBSS was used to wash the pellets. The final pellets were counted in a gamma counter to give the In value, while the supernatants from each washing were combined to give the Sur value.

Internalization values were represented in the form of the total internalized radioactivity (In) divided by the total surface-bound radioactivity (Sur) per million cells, defined herein as steady-state In/Sur. Steady-state values of In/Sur for cells of a given type in varying methocel media provide relative estimates of endocytosis rate for Tf-mediated endocytosis, particularly when it is assumed that Tf recycling rates are independent of the rheology of the extracellular media. Downregulation of surface-bound Tf receptor numbers is not expected for the duration of experiments given the preferential recycling of Tf receptors to the cell surface following internalization.

The role of extracellular viscosity on endocytosis rate.

As discussed herein, the viscosity of extracellular fluids influences the net endocytosis rate. Control of the extracellular viscosity affects the steady-state internalization of Tf receptor (bound to $^{125}$I-Tf) in K562 cells a human erythroleukemia cell line that has been commonly employed in Tf-mediated endocytosis studies [Schonhorn, J. E. and Wessling-Resnick, M. (1994) *Molecular and Cellular Biochein*. 135, 159–169], and can also affect Tf-mediated endocytosis in CHO (Chinese hamster ovary) cells transfected with human transferrin receptor [McGraw, T. E., Greenfield, L,. and Maxfield, F.R. (1987) *J. Cell Biol*. 105, 207–214]. These latter cells do not express functional endogenous hamster transferrin receptor, and provide a unique cell line to which results obtained with the K562 cells can be compared.

K562 cells were suspended in aqueous buffer medium containing between 0.0% to 1.8% methylcellulose (methocel). Rheological measurements (FIG. 1) indicate that this methocel concentration range endows the extracellular fluid with an apparent viscosity ranging from that of water to a viscosity exceeding that characteristic of the cell cytosol. The apparent viscosities (defined as measured shear stress over applied strain rate) of the methocels vary greatly depending upon the net force delivered to the cell membrane leading to pit formation. It is possible to show (see caption to FIG. 1) that the maximum force delivered by a cell on the extracellular fluid by invaginating pits ranges from approximately 1 to 10 Pa, depending upon whether clustering of receptors has occurred.

Figure 2:
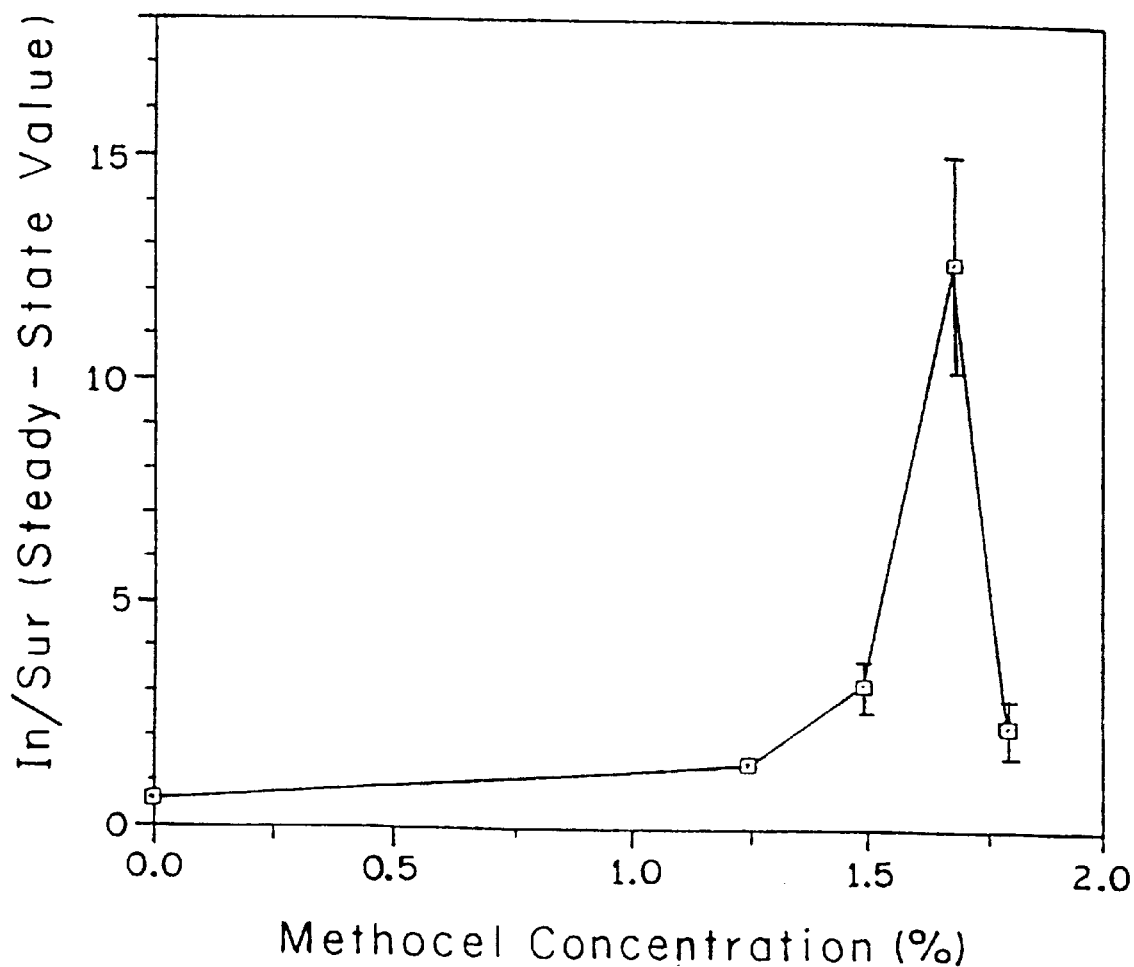
FIG. 2 shows steady-state values of total internalized $^{125}$I-Tf over total surface-associated $^{125}$I-Tf (In/Sur) for K562 cells suspended in methocel solutions of varying methocel concentration between 0 and 2%. Error bars represent mean standard error, with n=4.

FIG. 2 shows K562 steady-state internalization values of $^{125}$I-Tf as a function of methocel concentration. The endocytosis rate increases with increasing methocel concentration from 1.25% to 1.7%, beyond which the internalization rate sharply diminishes. The methocel solutions with methocel concentration greater than 1.25% possess an apparent viscosity near to, and potentially exceeding, that of the cell cytosol (FIG. 1), at least in the range of shear stresses relevant to RME. According to FIG. 1, increasing methocel concentration leads to an increase in the viscosity of the extracellular fluid (at fixed applied stress). This means that the difference between the intracellular and extracellular viscosity decreases as the methocel concentration is increased beyond 1.25%. As the difference between the intracellular and extracellular viscosity grows smaller, the initial membrane velocity toward the cytosol increases, coinciding with an increased endocytosis rate. This behavior is shown in FIG. 2 up to a methocel concentration of 1.7%. Increasing methocel concentrations above 1.7% leads to extracellular viscosities that exceed the intracellular viscosity. Accordingly, as the difference in viscosities increases, the rate of endocytosis decreases. As shown in FIG. 2, methocel concentrations above 1.7% cause a decrease in the rate of endocytosis. This decrease is consistent with the theory presented herein.

CHO cells were used to determine if the predicted behavior would occur in other cell lines. Similar protocols were used for the determination of steady-state In/Sur with the CHO cells as with the K562 cells. Endocytosis was studied in the CHO cells both with the cells adhered to a solid surface and in suspension. According to FIG. 3, In/Sur increases with methocel concentration up to a methocel concentration of 1.25% for the adhered cells (p=0.0011), and 1.5% of the suspended cells p=0.0148). Beyond these concentrations, a diminution of the internalization rate is observed for both the adhered (p=0.0146) and suspended (p=0.0872) cells. Possible sources of deviation in the In/Sur trends between the adhered and suspended CHO cells, as well as between the CHO and K562 cell lines, include variations in the apparent cell viscosity, cell membrane tension and exposed membrane area. For example, it has been shown that cell spreading increases intracellular tension [Want, N. and Ingber, D. E. 1994 *Biophys. J*. 66, 2181–2189]. This effect may play a role in the diminished rates of internalization observed in FIG. 3 for the adhered CHO cells. That each of the cell lines studied exhibits a signature rise in Tf internalization with increasing methocel concentration, followed by a diminution beyond a methocel concentration coinciding with an apparent extracellular viscosity near to that expected of the cell cytosol, is consistent with the theory presented herein.

EXAMPLE 2
Viscous Hydrogels with Optimum Viscosity for Vaginal Delivery of Leuprolide to Sheep A composition including methylcellulose (methocel) and leuprolide, which binds specifically to vaginal epithelial LHRH receptors, was administered to the vagina of sheep to demonstrate the utility of viscous hydrogels with optimally chosen rheological properties for dramatically improving the delivery of bioactive agents across mammalian epithelia.

The concentrations of the hydrogel were selected as 1.5% and 1.75% since, as can be seen from FIG. 1, the apparent viscosity of the methocels is in the range of between 2 and 200 or more Poise in the applied stress range of between 1 and 100 Pascals. Leuprolide was mixed in the hydrogels at a concentration of 20 μg/ml. Sheep were treated with a total of 100 μg leuprolide. Each treatment caused a significant increase in LH, as shown in FIG. 4. To demonstrate that leuprolide delivery is enhanced using the rheologically optimized methocels, control experiments were performed using the same dose (100 μg leuprolide) administered to the vagina of sheep in phosphate buffered saline (methocel 0.0).

The results of this comparison study are shown in FIG. 5. The results demonstrate that single-dose administration of leuprolide in a rheologically-optimized hydrogel could be used to regulate follicular development in humans and animals. Repeated daily administration would be expected to inhibit ovarian function.

EXAMPLE 3

Intranasal Administration of Gonadotropin Releasing Hormone ("GnRH") Analogs

A GnRH analog was intranasally administered to sheep using a highly viscous solution to demonstrate the generality of the compositions and methods presented herein for delivering macromolecules across mammalian epithelial barriers. A blueline umbilical cannula was inserted in the nostril of the sheep to a preset depth of 10 cm before delivery of a 1.5% methocel solution (5 mL solution, containing 100 μg GnRH analog) from a syringe. The serum concentration of LH was monitored as a function of time following administration. The results of this study are shown in FIG. 6. A therapeutically effective serum concentration of LH was obtained, which is comparable to that obtained via injection, reflecting the ability of the compositions and methods described herein to enhance transcellular transport of a GnRH analog. When a control of 5 mL saline containing 100 μg was administered, the serum concentration of LH was vinualy undetectable.

EXAMPLE 4

Comparison of Intravaginal Delivery and Intravenous Delivery of Vasopressin to Sheep Unlike leuoprolide, vasopressin (though of similar molecular weight as leuoprolide) does not bind to cell surface receptors of the vaginal epithelium. Accordingly, vasopressin (ADH) was adrinistered intravaginally to sheep to determine whether binding of the compound to be delivered to a receptor had an effect on the intracellular delivery. Effective delivery of vasopressin was measured by determining the systemic cortisol level.

As shown in FIG. 7, there was virtually no difference in systemic cortisol levels following administration of a control (an aqueous solution that did not contain methocel or vasopressin) relative to when 200 μg of vasopressin was delivered intravaginally in 1.5 or 1.75% methocel solutions. By comparison, systemic administration of vasopressin (IV administration) showed increased cortisol levels. This example demonstrates the importance of receptor binding to the success of the method.

Those skilled in the art will recognize, or be able to ascertain using no more than routine experimentation, many equivalents to the specific embodiments of the invention described herein. Such equivalents are intended to be encompassed by the following claims. The references cited herein are hereby incorporated by reference.

We claim:

1. A method for delivering agents to cells comprising administering to the cells a composition that includes a viscous material and an agent to be delivered, wherein the composition has an apparent viscosity between 10 and 2000 Poise and has approximately the same apparent viscosity, at a shear stress of between approximately 1 and 200 Pascal at a strain rate approximately that of endocytosis, as the cytosolic fluid of the cell to which the agent is to be delivered, and the agent is a bioactive or diagnostic agent selected from the group consisting of agents that interact with a receptor on the cell surface, agents attached to a molecule that interacts with a receptor on the cell surface, and agents incorporated in a carrier that is attached with a compound on its surface that interacts with a cell surface receptor.

2. The method of claim 1 wherein the quotient of (a) the apparent viscosity of the cytosol of the target cells minus the apparent viscosity of the composition and (b) the apparent viscosity of the cytosol of the target cells is between approximately −0.1 and 0.3.

3. The method of claim 2 wherein the quotient of (a) the apparent viscosity of the cytosol of the target cells minus the apparent viscosity of the composition and (b) the apparent viscosity of the cytosol of the target cells is between approximately 0 and 0.3.

4. The method of claim 3 wherein the quotient of (a) the apparent viscosity of the cytosol of the target cells minus the apparent viscosity of the composition and (b) the apparent viscosity of the cytosol of the target cells is between approximately 0 and 0.1.

5. The method of claim 4 wherein the quotient of (a) the apparent viscosity of the cytosol of the target cells minus the apparent viscosity of the composition and (b) the apparent viscosity of the cytosol of the target cells is between approximately 0 and 0.05.

6. The method of claim 1 wherein the apparent viscosity of the composition is between 50 and 200 Poise.

7. The method of claim 1 wherein the apparent viscosity of the composition is between 10 and 200 Poise.

8. The method of claim 1 wherein the agent is selected from the group consisting of proteins, peptides, carbohydrates, nucleic acid molecules, and chemotherapeutic agents.

9. The method of claim 8 wherein the agent is selected from the group consisting of honrones, attachment peptides, enzymes, coagulation inhibitors, cytokines, antibodies, antibody fragments, lectins, albumin, calcitonin, alpha-1-antitrypsin (A1A), deoxyribonuclease (DNAase), and lectins.

10. The method of claim 8 wherein the nucleic acid molecules are selected from the group consisting of DNA, RNA, antisense oligonucleotides, oligonucleotides which bind to various sites within the cells, oligonutcleotides which interact with various sites within the cells, triplex forming oligonucleotides, aptainers, ribozymes and ribozyme guide sequences.

11. The method of claim 8 wherein the chemotherapeutic agent is an anti-cancer drug.

12. The method of claim 1 wherein the agent is a diagnostic agent.

13. The method of claim 1 wherein the viscous material is selected from the group consisting of hydrogels, lipogels and sols.

14. The method of claim 13 wherein the hydrogel is selected from the group consisting of celluloses, polyalkyleneoxide, polyvinylpyrrolidone, dextrans, alginates, agaroses, gelatin, hyaluronic acid, trehalose, polyvinyl alcohol, and copolymers and blends thereof.

15. The method of claim 1 wherein the cell to which the agent is to be administered is in the nose, vagina, rectum, mouth, ear, eye, or lungs.

16. The method of claim 1 wherein the composition is administered topically.

17. The method of claim 1 wherein the composition is administered systemically.

18. The method of claim 1 wherein the composition comprises a carrier selected from the group consisting of viruses, liposoines, lipid/DNA complexes, micelles, potein/lipid complexes, nanoparticles, and microparticles.

19. A composition for administering compounds intracellularly comprising:

a viscous fluid and an agent to be delivered, wherein the composition has an apparent viscosity between 10 and 2000 Poise and has approximately the same apparent viscosity, at a shear stress of between approximately 1 and 200 Pascal at a strain rate approximately that of endocytosis, as the cytosolic fluid of the cell to which the agent is to be delivered, and the agent is a bioactive or diagnostic agent selected from the group consisting of agents that interact with a receptor on the cell surface, agents attached to a molecule that interacts with a receptor on the cell surface, and agents incorporated in a carrier that is attached with a compound on its surface that interacts with a cell surface receptor.

20. The composition of claim 19 comprising a carrier selected from the group consisting of viruses, liposomes, lipid/DNA complexes, micelles, protein/lipid complexes, nanoparticles, and microparticles.

21. The coinposition of claim 19 wherein the quotient of (a) the apparent viscosity of the cytosol of the target cells minus the apparent viscosity of the composition and (b) the apparent viscosity of the cytosol of the target cells is between approximately −0.1 and 0.3.

22. The composition of claim 21 wherein the quotient of (a) the apparent viscosity of the cytosol of the target cells minus the apparent viscosity of the composition and (b) the apparent viscosity of the cytosol of the target cells is between approximately 0 and 0.3.

23. The composition of claim 22 wherein the quotient of (a) the apparent viscosity of the cytosol of the target cells minus the apparent viscosity of the composition and (b) the apparent viscosity of the cytosol of the target cells is between approximately 0 and 0.1.

24. The composition of claim 23 wherein the quotient of (a) the apparent viscosity of the cytosol of the target cells minus the apparent viscosity of the composition and (b) the apparent viscosity of the cytosol of the target cells is between approximately 0 and 0.05.

25. The composition of claim 19 wherein the apparent viscosity of the composition is between 50 and 200 Poise.

26. The composition of claim 19 wherein the apparent viscosity of the composition is between 10 and 200 Poise.

27. The composition of claim 19 wherein the agent is selected from the group consisting of proteins, peptides, carbohydrates, nucleic acid molecules, and chemotherapeutic agents.

28. The composition of claim 27 wherein the peptide or protein is selected from the group consisting of hormones, attachment peptides, enzymes, coagulation inhibitors, cytokines, antibodies, antibody fragments, lectins, albumin, calcitanin, alpha-1-antitrypsin (A1A), deoxyribonuclease (DNAase), and lectins.

29. The composition of claim 27 wherein the genetic material is selected from the group consisting of DNA, RNA, antisense oligonucleotides, oligonlucleotides which bind to various sites within the cells, oligonucleotides which interact with various sites within the cells, triplex forming oligonucleotides, aptamers, ribozymes and ribozyme guide sequences.

30. The composition of claim 27 wherein the chemotherapeutic agent is an anti-cancer drug.

31. The composition of claim 19 wherein the agent is a diagnostic compound.

32. The composition of claim 19 wherein the viscous material is selected from the group consisting of hydrogels, lipogels and sols.

33. The composition of claim 32 wherein the hydrogel is selected from the group consisting of celluloses, polyalkyleneoxide, polyvinylpyrrolidone, dextrans, alginates, agaroses, gelatin, hyaluronic acid, trehalose, polyvinyl alcohol, and copolymers and blends thereof.

* * * * *

UNITED STATES PATENT AND TRADEMARK OFFICE
CERTIFICATE OF CORRECTION

| | | |
|---|---|---|
| PATENT NO. | : 5,985,320 | Page 1 of 1 |
| APPLICATION NO. | : 08/810275 | |
| DATED | : November 16, 1999 | |
| INVENTOR(S) | : David A. Edwards et al. | |

It is certified that error appears in the above-identified patent and that said Letters Patent is hereby corrected as shown below:

Column 1, lines 10-13, replace "The United State government has certain rights in this invention by virtue of government support under Grant Number NIH-5R01-GM26698 awarded by the National Institutes of Health." with --This invention was made with government support under Grant No. GM026698, awarded by the National Institutes of Health. The Government has certain rights in this invention.--

Signed and Sealed this
Eleventh Day of October, 2011

David J. Kappos
*Director of the United States Patent and Trademark Office*